US006489511B1

(12) United States Patent
Jones

(10) Patent No.: US 6,489,511 B1
(45) Date of Patent: Dec. 3, 2002

(54) AZOMETHINE COMPOUND MANUFACTURE

(75) Inventor: Garry D. Jones, Pittsford, NY (US)

(73) Assignee: Eastman Kodak Company, Rochester, NY (US)

(*) Notice: Subject to any disclaimer, the term of this patent is extended or adjusted under 35 U.S.C. 154(b) by 0 days.

(21) Appl. No.: 09/931,612

(22) Filed: Aug. 16, 2001

(51) Int. Cl.$^7$ .................... C07C 249/00; C07C 251/00; C07C 233/05
(52) U.S. Cl. .................. 564/168; 560/43; 564/440; 568/27; 568/36
(58) Field of Search ................. 564/168, 440; 560/43; 568/27, 36

(56) References Cited

U.S. PATENT DOCUMENTS 5,122,611 A  6/1992  Tanaka et al.

FOREIGN PATENT DOCUMENTS

JP  6-100790  *  4/1994

OTHER PUBLICATIONS

Korinek et al, Coll. Czec. Chem. Comm., vol. 44, pp 1460–1467, 1979.*

\* cited by examiner

*Primary Examiner*—Shailendra Kumar
(74) *Attorney, Agent, or Firm*—Arthur E. Kluegel

(57) ABSTRACT

Disclosed is a process for forming an azomethine compound, comprising:
 (a) reacting a compound "A" having an active methylene group or methine group with an arylprimaryamine compound "B";
 (b) in the presence of a base and an oxidizing agent and in a solvent medium containing a ketone compound having the formula $R^1C(O)R^2$ wherein $R^1$ and $R^2$ are independently C1–C4 alkyl groups;
 (c) at a temperature low enough to provide a yield of the azomethine product of at least 50 mole % based on compound A.

22 Claims, No Drawings

AZOMETHINE COMPOUND MANUFACTURE

FIELD OF THE INVENTION

This invention relates to a process for forming an azomethine compound, comprising reacting a compound having an active methylene group or methine group with an arylprimaryamine compound in the presence of a base and an oxidizing agent and in a solvent medium containing a ketone compound having C1–C4 alkyl groups at a temperature low enough to provide a yield of the azomethine product of at least 50 mole %.

BACKGROUND OF THE INVENTION

Chemical production ideally requires a process which offers high yield with minimal impact on the environment. These factors, along with careful choice of reagents, can lead to a low cost production process. The most widely used method for producing azomethine compounds consists of the oxidative condensation of an activated methylene or methine group containing compound "A" with an arylprimaryamine compound "B" in the presence of a base. Both one-phase and two-phase systems have been used.

One-phase systems typically require an organic solvent which adequately solubilizes the organic reactants. Examples which have been used are ethyl acetate, methylene chloride, and methanol. U.S. Pat. No. 5,122,611 describes a method for producing an azomethine dye which comprises oxidatively condensing an active methylene- or methine-containing compound, except those containing a sulfonic or carboxylic acid group, and p-phenylenediamine, except those containing a sulfonic or carboxylic acid group, in the presence of methylene chloride as a solvent under a basic condition. However, the organic reactants can require a large volume of such solvents to be adequately soluble. Lower molecular weight ketones such as acetone, would be thought to be a good choice for a solvent, as it typically has good solubility of the organic reactants and is also environmentally benign. However, these ketones appear to adversely affect the yields, presumably as a result of an unwanted side reaction. Therefore, ketones tend to be regarded as a problem as opposed to a potential solvent for such a reaction.

Two-phase systems (i.e. an organic and an aqueous phase) require that the organic solvent is not water miscible, which therefore limits the solvent choice to those such as methylene chloride (dichloromethane), ethyl acetate, toluene, heptane, propyl acetate, etc. However, to ensure adequate conversion to product, only more polar solvents such as methylene chloride or ethyl acetate can be used. The solvent of choice would be dichloromethane, but this solvent has strong environmental reasons for avoiding its use. Simple N-alkyl acetates would potentially be a good choice as solvent, but do not typically give such good separation of the organic phase from the aqueous phase, resulting in production problems. Also, in two-phase systems, the water phase adds considerable volume to the reaction, reducing productivity and requiring additional process steps for its removal.

It is a problem to be solved to provide a process for preparing an azomethine compound in good yield without significant environmental complications.

SUMMARY OF THE INVENTION

The invention provides a process for forming an azomethine compound, comprising:

(a) reacting a compound "A" having an active methylene group or methine group with an arylprimaryamine compound "B";

(b) in the presence of a base and an oxidizing agent and in a solvent medium containing a ketone compound having the formula $R^1C(O)R^2$ wherein $R^1$ and $R^2$ are independently C1–C4 alkyl groups;

(c) at a temperature low enough to provide a yield of the azomethine product of at least 50 mole % based on compound A.

The process provides good yield without creating environmental concerns associated with other solvent materials such as methanol and methylene chloride.

DETAILED DESCRIPTION OF THE INVENTION

The invention is generally described above. Compound A contains an active methylene (—$CH_2$—) group or methine (—CH<) group. Such compounds include, for example, those with an acylacetamide group such as a β-keto carboxamide group. Specific examples are an acyl acetanilide such as a benzoylacetanilide or a pivaloylacetanilide. These compounds are useful yellow dye-forming couplers in the photographic arena. The methine group may be substituted with an non carbon group such as a halogen, nitrogen, oxygen or sulfur linked group. Compound B is an arylprimaryamine. Typical of such compounds are 1° amine developing agents such as a phenylene diamine especially a paraphenylenediamine. As indicated hereinafter, these compounds may be substituted.

The reaction requires the co-presence of a base and an oxidizing agent and in a solvent medium containing a carbonyl compound having the formula $R^1C(O)R^2$ wherein $R^1$ and $R^2$ are independently C1–C4 alkyl groups. The base may be any basic material that provides a pH value in the desired range, typically 7 to 13.5. Most useful are the inorganic bases such as the carbonates, bicarbonates, and phosphates. Potassium carbonate is conveniently employed. Any oxidizing agent is suitably employed such as a persulfate. Ammonium persulfate is useful for this purpose. Although the amount of oxidizing agent may vary with the acylacetamide selected, suitable amounts are 0.9 to 4.0 equivalents to Compound A with 0.9–2.1 and 1.9–2.1 being typical. The ketone component is one with relatively short alkyl substituents, ranging up to 4 carbon atoms. Butanone and acetone are readily used with acetone (dimethylketone) being the most useful.

The reaction is carried out at a controlled temperature so that the yield is at least 50 mole % based on compound A. It has been found that temperatures above 25° C. cannot be expected to satisfy this requirement. In a preferred mode the temperature is less than 20° C. and more desirable form 4–12° C. With homologous ketones, slight variations in these temperature ranges can be expected.

The relative equivalents of Compound A to Compound B suitably range form 0.9 to 1.5 and more typically 0.9 to 1.1. The amount of base depends on the specific base and the specific type of acylacetamide employed and typically ranges from 2 (for a dibasic compound) to 30 per mole of compound A, with 4–6 typically employed. The reaction time is dependent on the rate of addition of oxidizing agent and is typically 0.5 to 12 hours with 1–8 and more usually, 2–6 hours being employed.

Typical examples of dyes that are conveniently made using the process of the invention have the following general formula I.

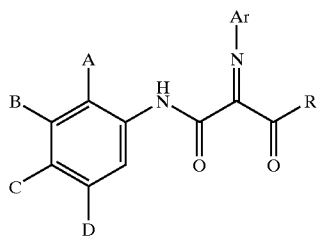
                                                                    I wherein
- A is chloro, C1–C4 alkoxy such as methoxy or isopropoxy, methyl or trifluoromethyl;
- B is H;
- C is H or chloro;
- D is H, chloro, carboxyl, sulfonamido, carbonamido, alkoxy, sulfamoyl or sulfonyl;
- R is a substituent such as an alkyl group, especially tertiary or methylcyclopropyl, or an aryl group such as a phenyl group; and
- Ar is suitably a group having the formula:

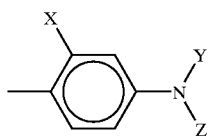

where X is H, or a methyl, methoxy or carbonamido group; and each Y and Z are H or an independently selected substituent group; provided that Y and Z may join to form a ring. Ar may also be

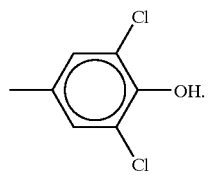

The following are examples that can be made in accordance with the process of the invention.

D1
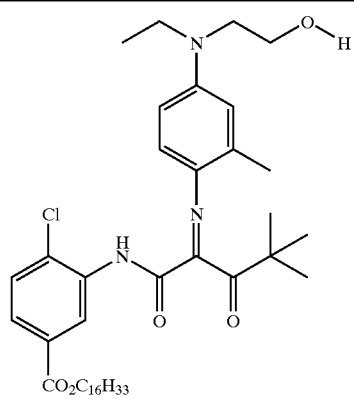

D2
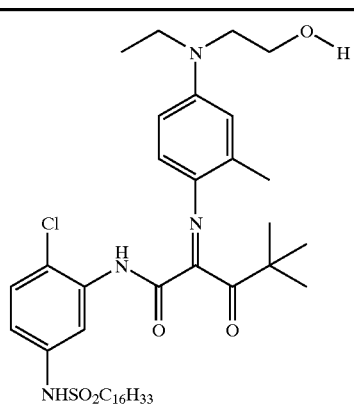

D3
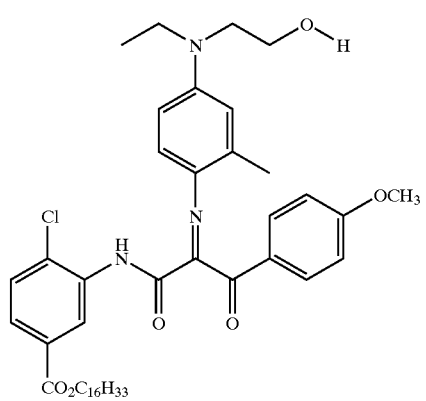

D4
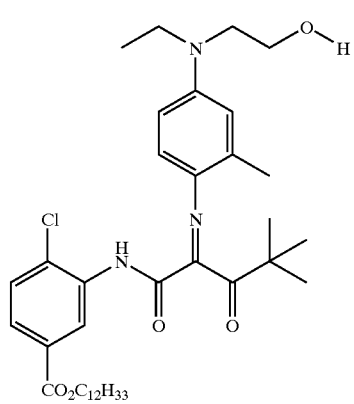

D5
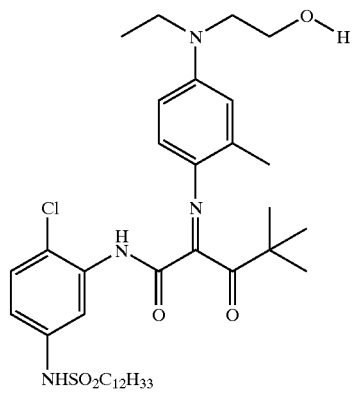

-continued

D6
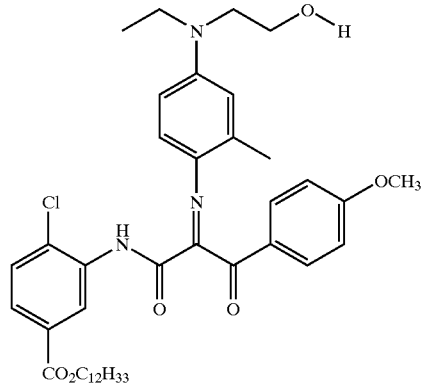

D7
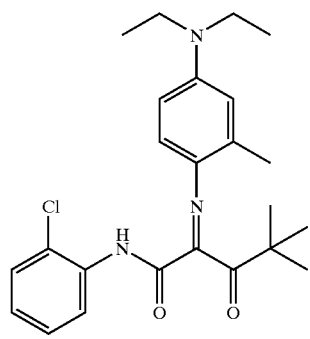

D8
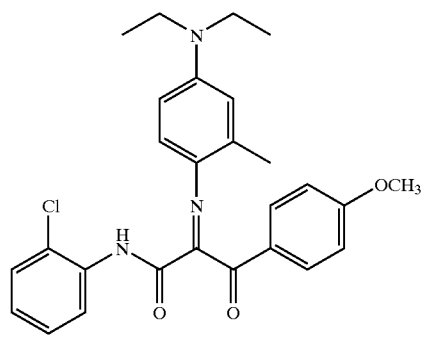

D9
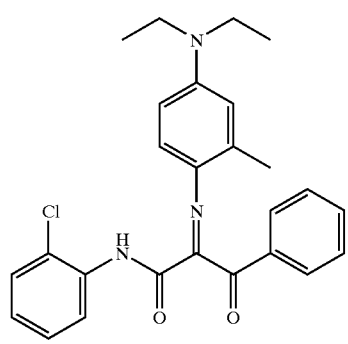

-continued

D10
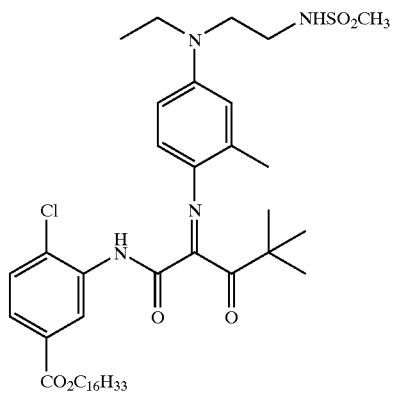

D11
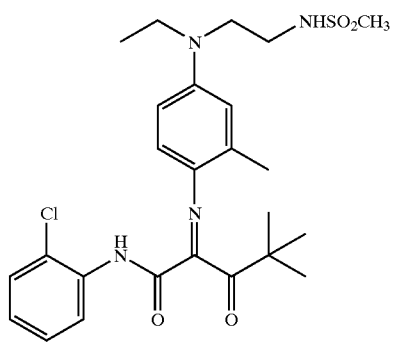

D12
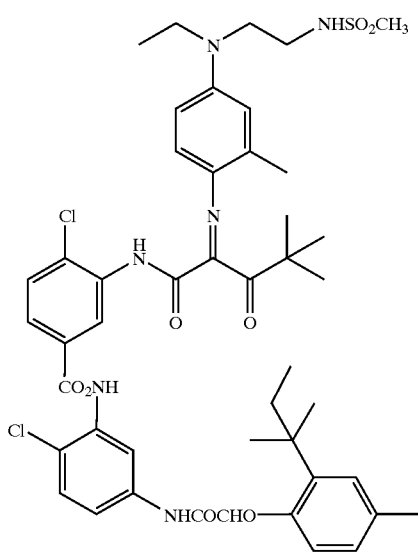

The reaction is carried out as a one-phase, heterogeneous reaction. The inorganic by-products can be filtered, with the product being soluble in the organic solvent. No water washes need to be performed in the work-up of the product. Other advantages of the process include lower solvent usage, safer inorganic bases, less reaction volume, simplified work-up, low impurity, and high yield.

Synthetic Scheme

The following is a scheme in accordance with the teachings of the invention.

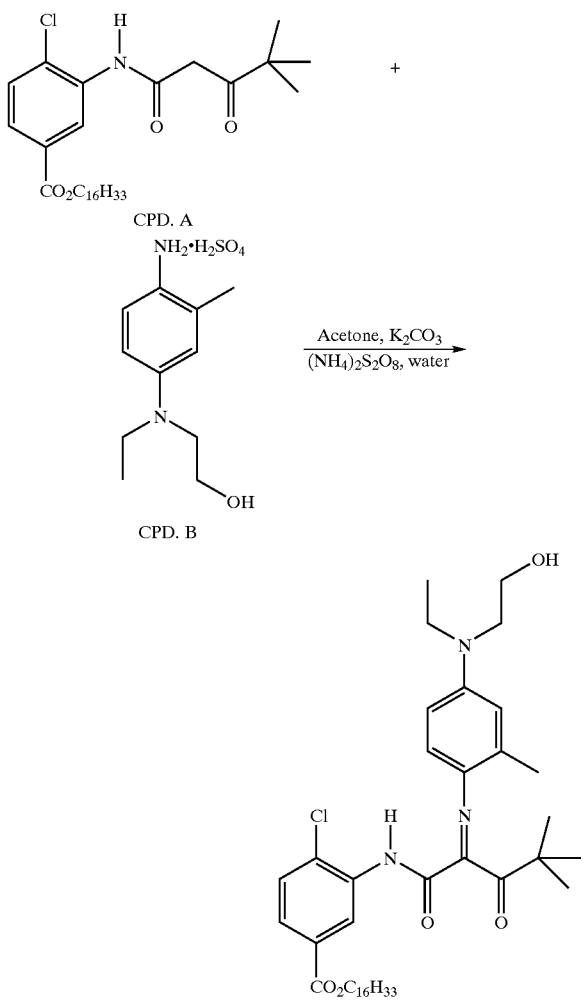

Synthesis Example

To a 500 ml round bottom flask was added Compound B (30.0 g, 0.057 mol) and acetone (180 g). The mixture was stirred at 350 rpm and heated to 30° C. Once a solution had formed, Compound A (17.13 g, 0.059 mol), potassium carbonate (43.67 g, 0.316 mol) and magnesium sulfate (22 g) were added The reaction mixture was then cooled to 10° C. and a solution of ammonium peroxydisulfate (26.22 g, 0.115 mol) in water (33 g) was slowly added to the reaction mixture over approximately 4 hours.

After addition of the ammonium peroxydisulfate solution, toluene (60 g) was added and the reaction mixture was heated to 40° C. The reaction mixture was then filtered to another 500 ml round bottom flask and the solvent removed in vacuo. Methanol (90 g) and citric acid (0.55 g, 0.003 mol) were added, the solution heated to reflux and then cooled to 10° C. The product was filtered, washed with methanol (60 g) and heptane (60 g) and the dried in a vacuum oven at 60° C. Product yield was 34.0 g, 83%. In the example, magnesium sulfate is used as it helps in the work-up procedure in production. To help remove residual metal ions, specifically $Mg^{2+}$, a small amount of citric acid is added to the crystallization solvent.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for its indicated utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)-hexanamido, alpha-(4-hydroxy-3-t-butylphenoxy)tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups.

The entire contents of the patents and other publications referred to in this specification are incorporated herein by reference.

What is claimed is:

1. A process for forming an azomethine compound, comprising:
   (a) reacting a compound "A" having an active methylene group or methine group with an arylprimaryamine compound "B";
   (b) in the presence of a base and an oxidizing agent and in a solvent medium containing a ketone compound having the formula $R^1C(O)R^2$ wherein $R^1$ and $R^2$ are independently C1–C4 alkyl groups;
   (c) at a temperature low enough to provide a yield of the azomethine product of at least 50 mole % based on compound A.

2. The process of claim 1 wherein the temperature of reaction is not more than 25° C.

3. The process of claim 2 wherein the temperature of reaction is not more than 20° C.

4. The process of claim 3 wherein the temperature of reaction is in the range of 4–12° C.

5. The process of claim 1 wherein the aryl group of compound B is a phenyl group.

6. The process of claim 1 wherein compound B is a p-phenylenediamine.

7. The process of claim 1 wherein compound A is a β-keto carboxamide.

8. The process of claim 7 wherein compound A is an acylacetanilide compound.

9. The process of claim 8 wherein compound A is a pivaloylacetanilide compound.

10. The process of claim 1 wherein the base is an inorganic base.

11. The process of claim 10 wherein the base is a carbonate.

12. The process of claim 1 wherein the ketone compound is acetone.

13. The process of claim 1 wherein the ketone compound is butanone.

14. The process of claim 1 wherein the ketone compound comprises substantially all of the solvent employed.

15. The process of claim 14 wherein the ketone compound is acetone.

16. The process of claim 14 wherein the ketone compound is butanone.

17. The process of claim 1 wherein the oxidizing agent is a peroxide compound.

18. The process of claim 17 wherein the oxidizing agent is a persulfate.

19. The process of claim 3 wherein compound A is an acylacetanilide compound, compound B is a p-phenylenediamine, and the carbonyl compound is acetone.

20. The process of claim 1 comprising the additional subsequent step of removing inorganic components by filtration without water washing.

21. The process of claim 17 comprising the additional subsequent step of removing one or more of the organic solvents by distillation.

22. The process of claim 18 comprising the additional subsequent step of removing undesired components by addition of an organic chelating agent.

* * * * *